(12) United States Patent
Sibbett

(10) Patent No.: US 7,906,026 B2
(45) Date of Patent: Mar. 15, 2011

(54) SIEVING MEDIA FROM PLANAR ARRAYS OF NANOSCALE GROOVES, METHOD OF MAKING AND METHOD OF USING THE SAME

(75) Inventor: Scott Sibbett, Corrales, NM (US)

(73) Assignee: Intel Corporation, Santa Clara, CA (US)

( * ) Notice: Subject to any disclaimer, the term of this patent is extended or adjusted under 35 U.S.C. 154(b) by 99 days.

(21) Appl. No.: 12/315,219

(22) Filed: Dec. 1, 2008

(65) Prior Publication Data

US 2009/0078616 A1    Mar. 26, 2009

Related U.S. Application Data

(62) Division of application No. 10/738,465, filed on Dec. 17, 2003, now abandoned.

(51) Int. Cl.
*B01D 15/34* (2006.01)
*B01D 63/08* (2006.01)

(52) U.S. Cl. ............ 210/659; 210/321.84; 210/500.26; 210/500.22; 422/101; 422/103; 977/701; 977/720; 977/723

(58) Field of Classification Search .................. None
See application file for complete search history.

(56) References Cited

U.S. PATENT DOCUMENTS

| | | | |
|---|---|---|---|
| 5,571,410 | A | 11/1996 | Swedberg et al. |
| RE36,113 | E | 2/1999 | Brueck et al. |
| 6,042,998 | A | 3/2000 | Brueck et al. |
| 6,233,044 | B1 | 5/2001 | Brueck et al. |
| 2002/0125192 | A1 | 9/2002 | Lopez et al. |
| 2003/0198130 | A1 | 10/2003 | Karp et al. |
| 2005/0103713 | A1 | 5/2005 | Ramsey et al. |

FOREIGN PATENT DOCUMENTS

| | | |
|---|---|---|
| CN | 1410155 A | 4/2003 |
| EP | 1319948 A2 | 6/2003 |
| WO | 96/12541 | 5/1996 |
| WO | 99/48599 | 9/1999 |
| WO | 02/28532 A2 | 4/2002 |

(Continued)

OTHER PUBLICATIONS

International Search Report (dated Aug. 4, 2005), International Application No. PCT/US2004/039642—International Filing Date Nov. 24, 2004 (20 pgs.).

(Continued)

*Primary Examiner* — Krishnan S Menon

(57) ABSTRACT

Disclosed herein are an apparatus and a method for separating molecules on the basis of size and or structure, and to a method of making the apparatus. Generally, the separation method includes passing a fluid comprising particles having different effective molecular diameters through a plurality of open, nanoscale channels disposed in surfaces of substrates. The method also includes obtaining a plurality of fractions of the passed fluid such that each of the fractions includes a major portion containing particles having similar size and shape and substantially free of particles having larger size and shape. The apparatus includes first and second substrates each of which has a surface containing a plurality of open, nanoscale channels disposed therein. The surfaces are bonded together such that each of the channels of the first substrate is in fluid communication with at least two of the channels of the second substrate and is misaligned relative to the channels of the second substrate. Interferometric lithography and anodic bonding or flip-chip bonding techniques can be used to make the apparatus.

13 Claims, 3 Drawing Sheets

FOREIGN PATENT DOCUMENTS

| WO | 02/065515 A2 | 8/2002 |
|---|---|---|
| WO | 03/035233 A1 | 5/2003 |
| WO | 2005062037 A3 | 7/2005 |

OTHER PUBLICATIONS

Marko T. Blom, et al., "On-Chip Hydrodynamic Chromatography Separated and Detection of Nanoparticles and Biomolecules", Analytical Chemistry, vol. 75, No. 24, Dec. 15, 2003, XP-001047360, ISSN: 0003-2700 (pp. 6761-6768).
Lux et al. (1990) J. High Resol. Cnrometogr. 13:436-437.
Guttman et al. (1990) Anal. Chem. 62:137-141.
Latham et al. (1993) Methods in Enzymology 225:473-489.
Corbett et al. (1994) Electrophoresis 15:1205-1211.
Effenhauser et al. (1994) Anal. Chem. 66:2949-2953.
Effenhauser et al. (1995) Anal. Chem. 67:2284-2287.
Schmalzing et al. (1997) Proc. Natl. Acad. Sci. USA 94:10273-10278.
Webster et al. (1996) "The Ninth Annual International Workshop on Micro Electro Mechanical Systems" pp. 491-496.
Von Heeren et al. (1996) J. Microcolumn Separations 8:373-381.
Peters et al. (1998) Anal. Chem. 70:2288-2295.
Turner et al. (1998) J. Vac. Sci. Technol.16:3835-3840.
He et al. (1998) Anal. Chern. 70:3790-3797.
Schmalzing et al. (1998) Anal. Chern. 70:2303-2310.
Duke et al. (1998) Phys. Rev. Let. 80:1552-1555.
Manabe et al. (1998) Electrophersis 19:2308-2316.
Desai et al. (1998) Biotechnology and Bioengineering 57:118-120.
Chou et al. (1999) PNAS 96:13762-13765.
Agrawal et al. (1999) Nature Biotechnology 17:412.
Han et al. (1999) Phys. Rev. Let. 83:1688-1691.
Yao et al. (1999) Proc. Natl. Acad. Sci. USA 96:5372-5377.
Han et al. (1999) J. Vac. Sci. Technol.17:2142-2147.
Hunt et al. (1999) Anal. Chem. 71 :2390-2397.
Liu et al. (1999) Anal. Chem. 71 :566-573.
Warren et al. (1999) SPIE 3878:185-192.
Han et al. (2000) Science 288:1026-1029.
Gygi et al. (2000) Current Opinion in Chemical Biology 4:489-494.
Ekstrom et al. (2000) Anal. Chem. 72:286-293.
Choe et al. 2000 Electrophoresis 21:993-1000.
Voss et al. (2000) Electrophoresis 21:2245-3350.
Gorg et al. (2000) Electrophoresis 21:1037-1053.
Hanash (2000) Electrophoresis 21:1202-1209.
Regnier (2000) J. High Resol. Chromatogr. 23:19-26.
Endo et al. (2000) Bioseparation Engineering pp. 69-74.
Svec et al. (2000) J. High Resol. Chromatogr. 23:3-18.
Yu et al. (2001) Anal. Chem 73:5088-5096.
Dulay et al. (2001) Anal. Chem. 73:3921-3926.
Monahan et al. (2001) Anal. Chem. 73:3193-3197.
Zuo et al. (2001) Electrophoresis 22:1603-1615.
Smilansky (2001) Electrophoresis 22:1616-1626.
Bousse et al. (2001) Anal. Chem. 73:1207-1212.
Cao et al. (2002) ADDI. Phys. Let. 81:174-176.
International Preliminary Report on Patentability for PCT/US2004/039642, mailed Jun. 29, 2006, 14 Pages.

SIEVING MEDIA FROM PLANAR ARRAYS OF NANOSCALE GROOVES, METHOD OF MAKING AND METHOD OF USING THE SAME

RELATED APPLICATIONS

This application is a Divisional of and claims priority to U.S. patent application Ser. No. 10/738,465, filed Dec. 17, 2003, entitled "Sieving media from planar arrays of nanoscale grooves, method of making and method of using the same," now pending, the disclosure of which is incorporated by reference in the disclosure of this application.

BACKGROUND OF THE DISCLOSURE

1. Field of Invention

The invention relates generally to an apparatus and method for separating molecules on the basis of size and/or structure, and to a method of making the apparatus.

2. Brief Description of Related Technology

It is important in the chemical and biological sciences to be able to separate different molecules from one another. Accurate and precise separation is especially important where the molecules are present in only a small volume solution, such as, for example, in the context of analytical and diagnostic testing. There remains a need to improve the efficiencies of such separations and, thereby, the convenience to researchers working in the chemical and biological sciences.

Generally, molecular separation techniques can include the use of a matrix (or membrane) where molecular transport and filtration occur perpendicular to the surface of the matrix. In such techniques, only those molecules having a precise, predetermined molecular weight and/or structure pass through the matrix. These separation techniques, however, are limited. For example, biomolecules may not be amenable to separation by such techniques because, for example, they may undesirably react with, or be rendered inactive by, the separating matrix. Even where biomolecules are amenable to these techniques, the separation can be imprecise, inaccurate, and/or difficult to reproduce due to batch-to-batch variations in the manufacture of the matrices. Poor separation efficiency and/or loss of sample volume also can be encountered.

In the biological sciences, gel fractionation or electrophoresis has been found to be a useful technique to separate and identify biomolecules such as, for example, proteins. Generally, in gel electrophoresis, the gel consists of a matrix of entangled polymer chains, intermixed with a buffer solution. A large number of interconnected pores are present within the matrix. A solution of proteins having a net electrical charge are placed in the matrix and travel through the pores under the influence of an electric field. Typically, a charged protein will move towards the pole with a charge opposite to that carried on the protein. The free-solution mobilities of denatured proteins are identical. In the presence of the gel matrix, however, protein mobilities tend to differ because the larger the protein, the more likely it will encounter a physical restriction in the matrix (either between or within the pores), thus retarding the protein's progress through the matrix relative to smaller proteins. The frictional force of the gel material acts as a protein sieve (or, more generally, a molecular sieve) separating the proteins by size. The rate at which a protein migrates through the electric field and gel matrix depends upon, for example, the strength of the field, size and shape of the protein, relative hydrophobicity of the sample in which the protein is present, and on the ionic strength and temperature of the buffer in which the protein is moving. Thus, as smaller proteins should move through the matrix faster than large proteins, the proteins become separated with fast moving bands of small proteins at the front and slow moving bands of larger proteins trailing behind.

One particular type of gel fractionation is two-dimensional (2-D) gel fractionation, which is useful for separating and identifying proteins in a sample by displacement in two dimensions oriented at right angles to one another. Two-dimensional gel fractionation is generally used as a component of proteomics and is a common step used to isolate proteins for further characterization by, for example, mass spectroscopy. This fractionation technique permits component proteins of the sample to separate over a larger area, increasing the resolution of each component protein. IEF (isoelectric focusing) and SDS-PAGE (sodium dodecyl sulfate polyacrylamide gel electrophoresis) comprise the two dimensions in a 2-D gel fractionation. In a first dimension, IEF fractionates biomolecules on the basis of pI values. In the subsequent, second dimension, SDS-PAGE further fractionates the previously-fractionated biomolecules based on size-charge ratios, which roughly correspond to a fractionation based on molecular weights.

Despite its widespread use, however, 2-D gel fractionation has its limitations. For example, it is not particularly good at resolving proteins or peptides having a low molecular mass as these often migrate through a polyacrylamide gel too rapidly. 2-D gel fractionation also is unsuitable for many proteins, such as hydrophobic proteins, because the proteins often interact with the gel matrix or otherwise undesirably react rendering subsequent analysis of the proteins difficult or impossible. Even when and where the proteins do not undesirably interact or react, it is often difficult to remove them from the gel, thus compromising the quality of any subsequent analysis of the protein. Another particular limitation is that the fractionation takes a long time to perform and requires extensive manual handling and attention, which makes it a long and laborious process requiring a skilled technician or scientist to master and perform. Performing the fractionation is very much an art, requiring much experimentation to find the correct conditions for sample preparation, focusing times, etc. Moreover, it is often difficult to reproduce the exact processing conditions under which multiple gels are made and, therefore, there can be inconsistencies between the various gels. Furthermore, gels can provide only limited resolution, which is often inadequate for certain molecular separation and analytical operations, and are often not re-usable. Still further, the gel material can disadvantageously degrade—polyacrylamide gel is a neurotoxin having a short shelf-life requiring that it be prepared just prior to use, and having properties that vary from batch to batch. Additionally, and given the foregoing limitations, the technique is often inadequate and/or wholly inappropriate for use in an integrated separation and analysis system. Though there have been advances to improve on certain of the foregoing limitations, many of the limitations still remain.

Alternatives to 2-D gel fractionation include techniques that utilize artificial gel media. In contrast to polyacrylamide gels where the sieving matrix is defined by random arrangement of long-chain polymers, the sieving matrix in artificial gels is defined by microfabrication and/or nanofabrication. Thus, the dimensions and topology of the sieving matrix in an artificial gel can be controlled and measured more precisely, and can be mass-produced more easily. For example, conventional photoresist-based lithography can be used to etch a pattern of obstacles on a silicon substrate (floor), which can be sealed with a glass or elastomeric ceiling layer to form a sieve through which a solution of molecules can be electrophoresed. Similarly, monolithic structures can be prepared with a sacrificial layer sandwiched between a dielectric floor and ceiling layers to define a working gap, wherein the sacrificial layer represents what will be the open space in the finished structure and, thus, the negative of the desired pattern of obstacles is etched into it. After the floor, ceiling, and retarding obstacles have been put in place, the sacrificial layer is removed by a wet chemical etch, leaving a working gap whose vertical dimensions are defined by the thickness of the removed layer. Due presumably to critical dimension limitations, however, only nucleic acid separations have been reported with these structures. Protein albumin is about four nanometers (nm) wide and about fifteen nanometers in length and, therefore, is too small to interact physically with patterned structures having 100 nm diameter pillars on a 200 nm pitch. Other techniques contemplate the use of electrochromatography, in situ casting of sieving media within preformed channels of a substrate, and the use of porous materials such as porous silicon as a porous media. Notwithstanding these advances, there remain limitations not adequately addressed in the art.

BRIEF DESCRIPTION OF THE DRAWINGS

For a more complete understanding of the disclosure, reference should be made to the following detailed description and accompanying drawings wherein.

Figure 1:
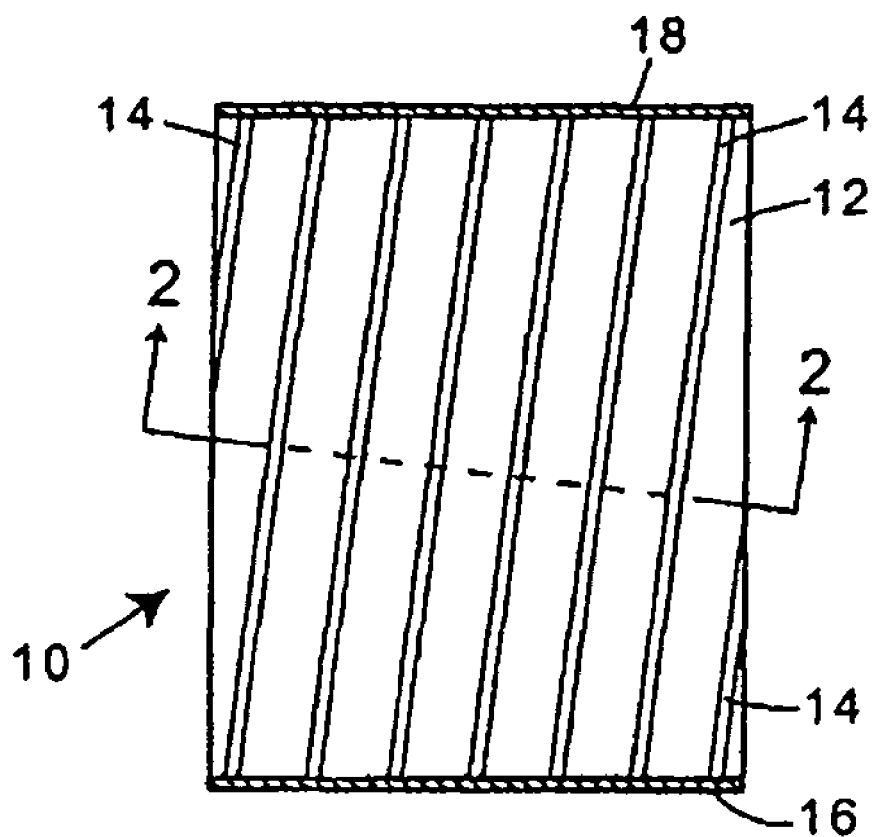
FIG. 1 is an enlarged, top view of a surface of a substrate having a plurality of nanoscale channels disposed therein.

While the disclosed apparatus and methods are susceptible of embodiments in various forms, there are illustrated in the drawings (and will hereafter be described) specific embodiments of the invention, with the understanding that the disclosure is intended to be illustrative, and is not intended to limit the invention to the specific embodiments described and illustrated herein.

DETAILED DESCRIPTION OF THE PREFERRED EMBODIMENTS

As used herein the term "nanoscale channel" refers to any void space in a surface of a substrate having a diameter in at least one direction of about one to about 500 nm. When referring to the channel, the term "diameter" is used in its ordinary sense, i.e., the distance across and through the middle of the channel, perpendicular to the axis of the channel, and parallel to the plane of the substrate in which the channel is disposed. When referring to a channel(s), however, the term "diameter" is not intended to limit the cross-sectional shape of the channel(s) to a circle, as any channel shape can be employed. Thus, the term "diameter" as used herein also includes "equivalent diameter" as defined in Table 5-8 of "Perry's Chemical Engineers' Handbook," at p. 5-25 (6$^{th}$ Ed., 1984) (see also 7$^{th}$ Ed., 1997, at pp. 6-12 to 6-13). As used herein, the term "array" refers to any arrangement of nanoscale structures or channels.

Disclosed herein is an apparatus comprising first and second substrates, each of the substrates having a surface containing a plurality of open, nanoscale channels disposed therein. The surfaces are bonded together such that each of the channels of the first substrate is in fluid communication with at least two of the channels of the second substrate and is misaligned relative to the channels of the second substrate.

The channels can have equivalent and constant cross-sectional areas within a range of about one square nanometer (nm$^2$) to about 10,000 nm$^2$, and more preferably, about 10 nm$^2$ to about 1000 nm$^2$. Alternatively, the channels can have equivalent and variable cross-sectional areas within a range of about 1 nm$^2$ to about 10,000 nm$^2$, and more preferably, about 10 nm$^2$ to about 1000 nm$^2$. Thus, in such an embodiment, a first portion of the channel can have a cross-section areas of about 10,000 nm$^2$, for example, while a second portion of the channel can have a cross-sectional areas of about 1 nm$^2$, for example. Benefits of such variable cross-sectional areas within the same channel can be realized when resolution of various, different-sized particles is desired. The channels within each substrate should be parallel to each other and should traverse an entire length of the surface in which they are disposed. Preferably, the channels within each substrate are spaced equidistant from each other, though they need not be. Given the cross-sectional areas of the channels and the intended use of the apparatus, each of the surfaces in which the channels are disposed preferably contains at least about 1000 channels to about ten million channels.

Generally, the substrates can be constructed of any material that is amenable to patterning of nanoscale channels and capable of being bonded together. Preferably, however, the first and second substrates can be made from one or more materials selected from the group consisting of quartz, silica, silicon, porous silicon, polysilicon, and porous polysilicon. More preferably, one of the materials of construction is quartz. Suitable silicon materials include porous silicon.

The apparatus preferably also includes third and fourth substrates bonded to edge surfaces of each of the first and second substrates. The edge surfaces should be substantially perpendicular to the channels.

Preferably, the third and fourth substrates can be made from one or more materials selected from the group consisting of quartz, silica, silicon, porous silicon, polysilicon, porous polysilicon, and silicon oxynitride. More preferably, one of the materials of construction is silicon oxynitride.

As previously noted, each of the channels of the first substrate is misaligned relative to the channels of the second substrate. The misalignment can be defined by an angle, which itself is defined by an intersection of a channel of the first substrate and a channel of the second substrate. Preferably, the channels of the first substrate are misaligned relative to the channels of the second substrate by an angle of about 0.05° to about 45°, more preferably about 0.05° to about 15°, highly preferably, about 0.1° to about 10°, and even more highly preferably about 0.5° to about 5°.

Generally, the apparatus can be made by patterning an array of open, nanoscale channels on a major planar surface of each of a first substrate and a second substrate. The channeled surfaces can be bonded together such that each of the channels of the first substrate is in fluid communication with at least two of the channels of the second substrate, and such that the each of the channels of the first substrate is misaligned relative to the channels of the second substrate. A preferred method of bonding includes suitable flip-chip bonding methods. Edge surfaces of each of the bonded first and second substrates can be capped with one or more cap substrates bonded to each edge surface, wherein the edge surfaces are substantially perpendicular to the channels.

There are numerous suitable methods of patterning an array of open, nanoscale channels on a surface of a substrate. Examples of such suitable methods include lithography methods such as, for example, interferometric lithography ("IL"), immersion interferometric lithography, electron beam lithography, scanning probe lithography, nanoimprint, extreme ultraviolet lithography, and X-ray lithography. Generally, IL is a preferred method of patterning the nanoscale channels.

Generally, lithography is a highly-specialized printing process used to create detailed patterns on a substrate, such as a silicon wafer. An image containing a desired pattern is projected onto the wafer, which is coated by a thin layer of photosensitive material called "resist". The bright parts of the image pattern cause chemical reactions which, in turn, render the resist material soluble, and, thus, dissolve away in a developer liquid, whereas the dark portions of the image remain insoluble. After development, the resist forms a stenciled pattern across the wafer surface, which accurately matches the desired pattern. Finally, the pattern is permanently transferred into the wafer surface, for example by a chemical etchant, which etches those parts of the surface unprotected by the resist.

Interferometric lithography ("IL") generally refers to a process of lithography where two or more mutually coherent light waves (or beams) interfere to produce a standing wave, which can be recorded in a photoresist. More specifically, in IL, a sinusoidal standing wave pattern of light intensity is produced by interference at the region of intersection of two coherent light beams. A photoresist-coated substrate positioned at the point of intersection undergoes exposure, printing a periodic, line-space pattern whose period (P) is determined by the wavelength of light ($\lambda$) and the angle of intersection (A) of the light beams (i.e., $P=\lambda/2 \sin(A)$). The angle (A) should be sufficiently large to produce an interference pattern that has a high spatial frequency. The resulting interference pattern should have nanoscale dimensions.

Examples of suitable IL techniques that can be used to pattern the array of channels are described in, for example, Brueck et al. U.S. Pat. No. 5,705,321. Generally, the photoresist-coated substrate is prepared by depositing a thin, etch-mask layer on a silicon substrate (wafer); then depositing a thin, photoresist layer on top of the etch-mask layer. Thereafter, the photoresist layer is exposed to the periodic pattern of lines using fine-line IL optimized to yield the appropriate nanoscale dimension of unexposed photoresist. The photoresist is developed to remove the exposed photoresist. The photoresist pattern is next transferred into the etch-mask using an etching process (over-etching the etch-mask at this point can undesirably undercut the etch mask and further narrow the etch mask pattern). The remaining photoresist is then removed. A highly anisotropic etching process, such as with potassium hydroxide, for example, can be used to etch the exposed substrate (e.g., a silicon (Si) substrate), in which case the lines of the periodic pattern should be aligned with the {111} Si directions prior to photoresist exposure. In this process, the {111} Si surfaces are almost totally unetched and, thereby leave very narrow, quantum-sized Si walls with a very high aspect ratio. If reactive-ion or ion-milling etch processes are used instead of potassium hydroxide, then it is not necessary to pre-align the pattern with the {111} Si directions. The remaining etch mask then can be removed, leaving an all Si surface, which can be oxcized. The same basic method can be used to fabricate more complex structures by the use of multiple-exposure IL and/or combining IL with conventional optical lithography either during the photoresist exposure step or within multiple iterations of portions of the process.

The complex interference pattern produced on the photoresist layer or layers can be varied by rotating and/or translating the substrate, changing the angle (A), varying the number of exposures and/or the optical intensity, using a phase-amplitude mask in one or both illuminating beams of coherent radiation, and any combination of the foregoing. Further flexibility can be attained by a combination of any of the foregoing variations along with suitable optical imaging lithography techniques.

Though there are many suitable methods of patterning the nanoscale channels, IL represents one of the more convenient and preferred methods of patterning nanostructured features because it can be used to generate the entire pattern in one, parallel step and is not a serial writing technique. Other parallel techniques (e.g., imprint lithography) rely upon a primary patterning technique to generate a master that subsequently can be used to produce replicas of nanostructured features in a parallel fashion. The use of IL to pattern an array of nanoscale channels has additional advantages over other techniques (such as traditional acrylamide gel polymerization) since it is capable of creating highly-ordered structures, provides the possibility of creating macroscopic arrays of continually varying size or chemistry across one dimension, is highly reproducible, can be carried out rapidly over larger macroscopic areas at low cost (low relative to electron-beam lithography, for example), and can be more easily implemented in the creation of complex, integrated separation systems that are disposable or reusable. Furthermore, the use of lithographically-defined-separation matrices lends itself to simple implementation of these matrices into multi-level, 3-dimensional separation devices in which different screening mechanisms allow enhanced separations. Additionally, IL can be used to easily generate arrays of nanostructures (protrusions or channels) whose dimensions vary semi-continuously in the plane of surface of the material being patterned. Once the surface of the substrate has been patterned with the desired pattern of nanoscale channels, the patterned surfaces is bonded with another similarly patterned surface. Thus, the formed apparatus aims to eliminate some of the current limitations by the fabrication of highly-uniform and accurately-reproducible nanoscale separation systems prepared by nano- and microlithography.

A purpose in bonding the substrates together is to create intimate, physical contact between the surfaces of the substrates such that the solution and any particles therein that are traversing the channels remain confined to the void space defined by the channels. Suitable methods of bonding the patterned (or channeled) surfaces together include, but are not limited to, anodic bonding methods and flip-chip bonding methods capable of mating the surfaces such that each of the channels of the first substrate is in fluid communication with at least two of the channels of the second substrate, and such that the each of the channels of the first substrate is misaligned relative to the channels of the second substrate. Both anodic bonding and flip-chip bonding methods are known by those skilled in the art. Generally, flip-chip bonding (also known in the art as direct chip attach (DCA)) is a direct electrical connection of face-down ("flipped") electronic components onto substrates, circuit boards, or carriers, by mean of conductive bumps on chip bond-pads. In contrast, wire bonding uses face-up chips with a wire connection to each chip bond-pad.

Flip-chip bonding typically comprises bumping a first substrate (or wafer), attaching the bumped substrate to a second substrate, and filling any remaining void space between surfaces of the substrate with a filler material, such as an electrically-non-conductive material, keeping in mind that the filler material should not fill the channels of the substrate. In the electronics arts, the bump can serve many purposes, such as providing a path for transferring an electric charge or heat from one substrate to another. Here, however, the bump advantageously provides a mechanical mounting to assist in attaching one substrate to another. The bump can be prepared by a variety of methods including, for example, those using solder or stud-bumping techniques, vacuum deposition, electroplating, and adhesives. Flip-chip bonding is advantageous because if offers a high-speed, low-cost assembly method and results in a suitably rugged bond. Given the flip-chip bonding processing conditions, and the intended use of the formed apparatus, one skilled in the art can appropriately select the materials of construction for use in bonding the various substrates together.

As noted herein, cap substrates can be bonded to edge surfaces of the already-bonded first and second substrates to prevent the sample solution from entering or exiting the exposed edges of the apparatus in a direction parallel to the nanoscale channels, and to constrain the solution into and out of the apparatus in a direction roughly perpendicular to the direction of the channels. Generally, the cap surface is constructed of silicon oxynitride. The cap surface can be bonded with the aid of an adhesive suitable for attaching a silicon oxynitride surface, for example, to the edge surfaces of the already-bonded first and second substrates.

Once the cap substrates have been appropriately bonded to the edge surfaces, the apparatus can be suitably attached to or otherwise incorporated into a device capable of introducing an electric field and a solution of molecules.

The end result of these manufacturing steps is an apparatus whose nanoscale channels are freely accessible to solution added along the uncapped edges of the 2-chip stack. Hence, conventional electrophoresis and other forms of chromatography can be performed within the nanochannels. The apparatus can be used by filling the interior space (e.g., via capillary action) with a solution containing the molecules to be separated, and then applying an electric field along a direction roughly perpendicular to the channels. As previously noted, a charged molecule will migrate with (or against) the general direction of this applied field. The actual path of any given charged molecule will be quite torturous, as explained hereinafter.

Figure 2:
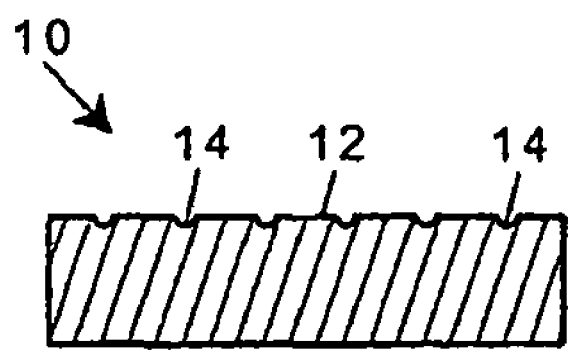
FIG. 2 is an enlarged, cross-sectional view of the substrate taken along line 2-2 in FIG. 1.

Referring now to the drawing figures, wherein like reference numbers refer to the identical or similar elements in the various figures, FIG. 1 is an enlarged, top view of a surface of a substrate having a plurality of nanoscale channels disposed therein. More specifically, FIG. 1 shows a substrate 10 having a surface 12 on or within which are disposed nanoscale channels 14. Edge surfaces (not shown) of the substrate 10 are capped with cap substrates 16 and 18. As shown in FIG. 1, each of the channels 14 has a constant cross-sectional diameter and each appears to be spaced equidistant from one another. as previously noted, the channels need not have a constant cross-sectional diameter or be spaced equidistant from one another. FIG. 2 is an enlarged, cross-sectional view of the substrate 10 taken along line 2-2 in FIG. 1.

Figure 3:
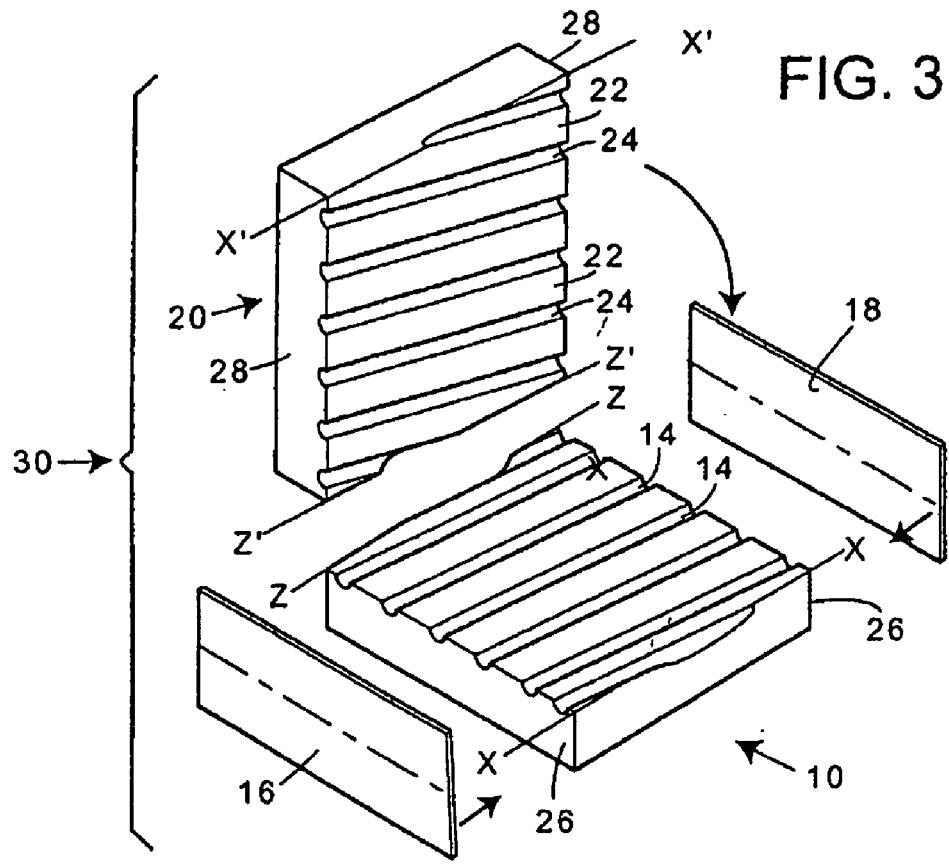
FIG. 3 is an enlarged, exploded view of a portion of an apparatus showing its constituent parts.

FIG. 3 is an enlarged, exploded view of a portion of an apparatus 30 showing its constituent parts. As shown, the apparatus 30 includes the substrate 10 and a second substrate 20 having a surface 22 on or within which are disposed nanoscale channels 24. Edge surfaces 26 and 28 of the substrates 10 and 20, respectively, are capped with cap substrates 16 and 18. When the substrates 10 and 20 are mated, the apparatus 30 is formed as edges X-X' and Z-Z' meet and cap substrates 16 and 18 are bonded to the edge surfaces 26 and 28.

Figure 4:
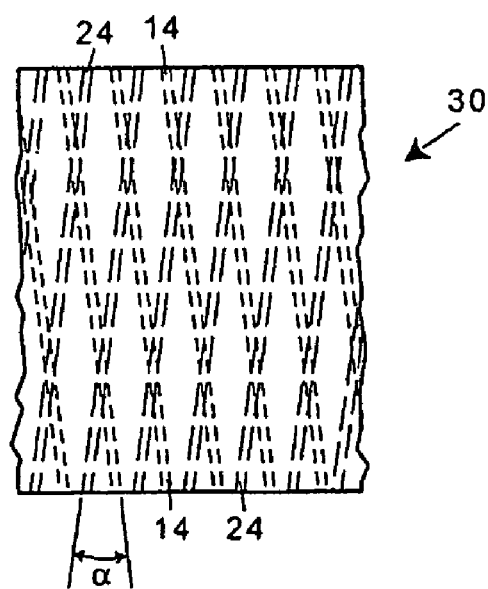
FIG. 4 is an enlarged, fragmentary plan view of the apparatus with the nanoscale channels disposed in each substrate shown in phantom; and, FIG. 5 is an enlarged, cut-away view of the apparatus showing the path of a material traversing the nanoscale channels.

FIG. 4 is an enlarged, fragmentary plan view of a portion of the formed apparatus 30 with the nanoscale channels 14 and 24 disposed in each substrate shown in phantom. As shown, each of the channels 14 of the first substrate 10 is misaligned relative to each channel 24 of the second substrate 20. The misalignment is defined in FIG. 4 by an angle ($\alpha$), which itself is defined by the intersection of a channel 14 of the first substrate 10 and a channel 24 of the second substrate 20.

Figure 5:
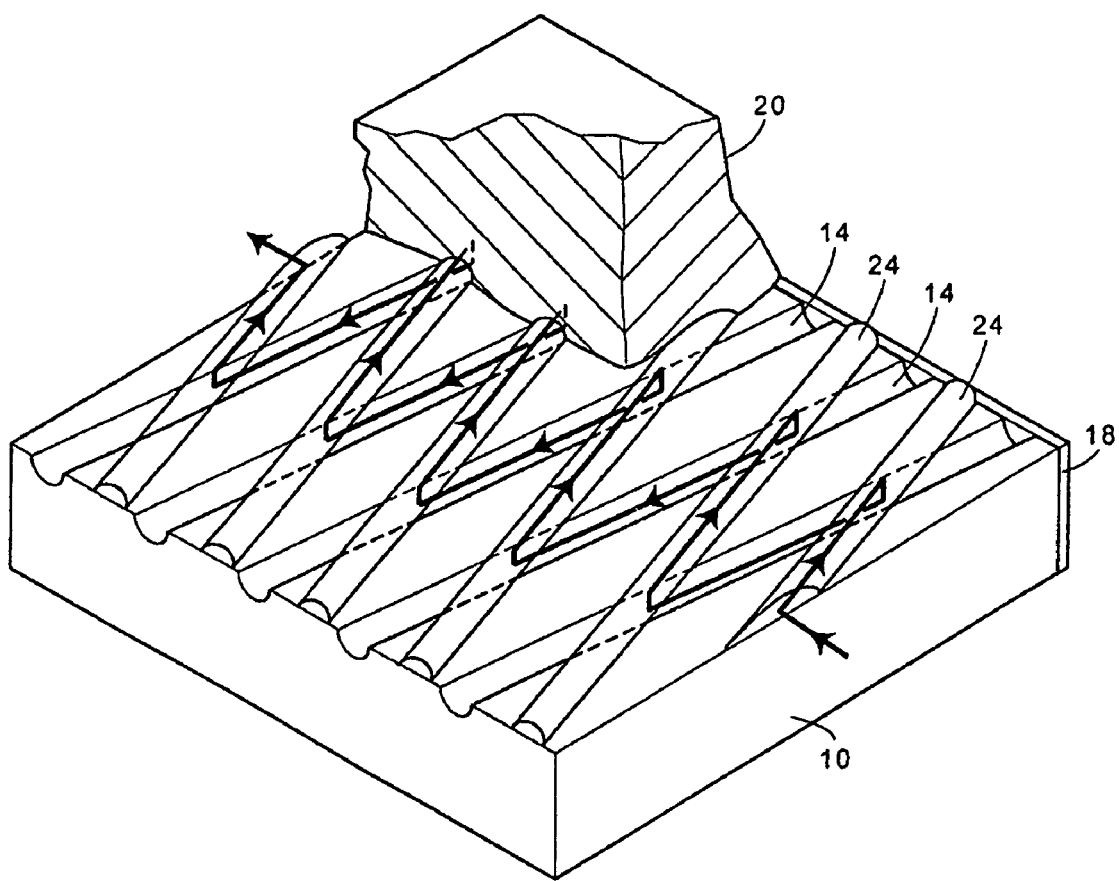

FIG. 5 is an enlarged, cut-away view of the apparatus showing the path of a material traversing the nanoscale channels 14 and 24, as depicted by the arrows. More specifically, shown in FIG. 5 is the apparatus 30 comprising the mated substrates 10 and 20, and the nanoscale channels 14 and 24 disposed therein. With the application of a force, such as a pressure or an electric field, molecules within a solution (depicted by the arrows in FIG. 5) can traverse the tortuous path created by the nanoscale channels 14 and 24. Moreover, the molecules are constantly zig-zagging through an interior space comprised almost entirely of wedge-shaped cracks. These cracks are the molecular-scale physical constrictions that impart a sieving capability to the 2-chip stack. The speed at which a particular molecule traverses from one end of the apparatus 30 to the other will, of course, depend upon the molecular weight and structure, as described above.

The formed apparatus is useful to resolve the various molecules present in a solution. Higher resolution can be obtained where the apparatus is used in combination with any one or more of the following mechanisms: affinity interaction (molecular recognition), asymmetric diffusion, electrophoretic mobility, entropic trapping, hydrophobic interaction, isoelectric point, and size exclusion.

The disclosed apparatus is useful to separate particles within a fluid having different effective molecular diameters into discrete portions characterized by common effective molecular diameter. Such particles are separated on the basis of the ability of particles having a smaller effective molecular diameter to pass through the apparatus channels more quickly than those having larger effective molecular diameters. Where particles have substantially equivalent molecular diameters, those molecules that are shorter in length should pass through the apparatus more quickly than those molecules that are longer in length. Higher resolution can be obtained where the apparatus is used in combination with any one or more of the following mechanisms: affinity interaction (molecular recognition), asymmetric diffusion, electrophoretic mobility, entropic trapping, hydrophobic interaction, isoelectric point, and size exclusion.

Suitable fluids that can pass through the apparatus include biologically derived materials such as, for example, peptides, polypeptides, proteins, antigens, antibodies, nucleotides, oligonucleotides, polynucleotides, aptamers, DNA, RNA, carbohydrates, complexes thereof, and suitable buffers. Fluids also can include non-biologically-derived materials such as, for example, synthetic polymers.

A buffer is a defined solution that resists change in pH when a small amount of an acid of base is added or when the solution is diluted. For example, the pH of the blood in a healthy individual remains remarkably constant at 7.35 to 7.45 because the blood contains a number of buffers that protect against pH change due to the presence of acidic or basic metabolites. From a physiological viewpoint, a change of +0.3 or −0.3 pH unit can be considered to be extreme. Many biological reactions of interest occur in the pH range of 6 to 8. Specific enzyme reactions that might be used for analyses may occur in the pH range of 4 to 19 or even greater. Thus, buffers are very useful for maintaining the pH at an optimum value. The proper selection of buffers for the study of biological reactions or for use in clinical analyses can be critical in determining whether of not they influence the reaction.

Proteins are amphoteric compounds; their net charge therefore is determined by the pH of the medium in which they are suspended. In a solution having a pH above the protein's isoelectric point, a protein has a net negative charge and migrates towards the anode in an electrical field. Below its isoelectric point, the protein is positively charged and migrates towards the cathode. The net charge carried by a protein is independent of its size, meaning that the charge carried per unit mass (or length, given proteins and nucleic acids are linear macromolecules) of molecule differs from protein to protein. Thus, at a given pH and under non-denaturing conditions, the electrophoretic separation of proteins is determined by both size and charge of the molecules. In contrast to proteins, nucleic acids remain negative at any pH used for electrophoresis and carry a fixed negative charge per unit length of molecule, provided by the phosphate group of each nucleotide of the nucleic acid. Thus, electrophoretic separation of nucleic acids proceeds strictly according to size.

Sodium dodecyl sulphate (SDS) is an anionic detergent that is used to denature proteins by "wrapping around" the polypeptide backbone of proteins—and SDS binds to proteins fairly specifically in a mass ratio of about 1.4:1. In so doing, SDS confers a negative charge to the polypeptide in proportion to its length (the denatured polypeptides become "rods" of negative charge cloud with equal charge or charge densities per unit length). It is usually necessary to reduce disulphide bridges in proteins before they adopt the random-coil configuration necessary for separation by size, such as, for example, with 2-mercaptoethanol or dithiothreitol. In denaturing SDS-based separations, therefore, migration is determined not by intrinsic electrical charge of the polypeptide, but by molecular weight.

Thus, if a mixture of SDS-complexed proteins in a suitable buffer is electrophoresed through the 2-chip stack, the larger the protein, the more likely it will encounter a restriction, and hence be retarded relative to a smaller protein. Proteins will elute from the chip in the order of size, the smallest first, and the largest last. The separated proteins can be further analyzed as desired.

The foregoing description is given for clearness of understanding only, and no unnecessary limitations should be understood therefrom, as modifications within the scope of the disclosure may be apparent to those having ordinary skill in the art.

What is claimed is:

1. A method comprising:
(a) passing a fluid comprising different components having different effective molecular diameters from end to end of an apparatus having at least about 1000 to about ten million open, nanoscale channels disposed in surfaces of a first and second substrates, the first and second substrates bonded together such that each of the channels of the first substrate is in fluid communication with at least two of the channels of the second substrate and is misaligned relative to the channels of the second substrate, and each of the channels of the second substrate is in fluid communication with at least two of the channels of the first substrate, and wherein the fluid communication between channels creates a continuous nonlinear pathway in which the fluid passes alternatingly between the channels of the first substrate and the channels of the second substrate;
(b) obtaining different fractions of the passed fluid, each of the fractions comprising a major portion comprising components having similar size and shape and substantially free of components having a different size and shape wherein the size and shape of the major portion of components of each of the fractions is different from the size and shape of the major portions of the components of the other fractions.

2. The method of claim 1, wherein the channels have equivalent and constant cross-sectional areas within a range of about 1 square nanometers ($nm^2$) to about 10,000 $nm^2$.

3. The method of claim 1, wherein the channels have equivalent and variable cross-sectional areas within a range of about 1 $nm^2$ to about 10,000 $nm^2$.

4. The method of claim 1, wherein each of the channels traverses an entire length of the surface.

5. The method of claim 1, wherein the channels of the first substrate are parallel to each other, and the channels of the second substrate are parallel to each other.

6. The method of claim 1, wherein the channels of the first substrate are spaced equidistant from each other, and the channels of the second substrate are spaced equidistant from each other.

7. The method of claim 1, wherein the first and second substrates comprise one or more materials selected from the group consisting of quartz, silica, silicon, porous silicon, polysilicon, and porous polysilicon.

8. The method of claim 7, wherein the first and second substrates comprise quartz.

9. The method of claim 5, further comprising third and fourth substrates bonded to edge surfaces of each of the first and second substrates, the edge surfaces being substantially perpendicular to the channels.

10. The method of claim 9, wherein the third and fourth substrates comprise one or more materials selected from the group consisting of quartz, silica, silicon, porous silicon, polysilicon, porous polysilicon, and silicon oxynitride.

11. The method of claim 10, wherein the third and fourth substrates comprise silicon oxynitride.

12. The method of claim 1, wherein the channels of the first substrate are misaligned relative to the channels of the second substrate by an angle of about 0.05° to about 45°, the angle defined by an intersection of a channel of the first substrate and a channel of the second substrate.

13. The method of claim 1, wherein one or more of the substrates additionally includes electrodes capable of creating an electric field along at least a portion of the nonlinear path traveled by a liquid passing through the continuous nonlinear pathway.

* * * * *